United States Patent [19]
Kleber et al.

[11] 4,259,078
[45] Mar. 31, 1981

[54] HEAT-STABLE QUATERNARY AMMONIUM COMPOUNDS FOR FIBER LUBRICATING

[75] Inventors: Rolf Kleber, Neu-Isenburg; Heinz Müller, Burgkirchen, both of Fed. Rep. of Germany

[73] Assignee: Hoechst Aktiengesellschaft, Fed. Rep. of Germany

[21] Appl. No.: 45,605

[22] Filed: Jun. 5, 1979

Related U.S. Application Data

[63] Continuation of Ser. No. 855,744, Nov. 29, 1977, abandoned.

[30] Foreign Application Priority Data

Dec. 3, 1976 [DE] Fed. Rep. of Germany ....... 2654794

[51] Int. Cl.³ .................... D06M 1/00; D06M 13/34
[52] U.S. Cl. ................... 8/115.6; 8/116 P; 8/188; 252/8.8
[58] Field of Search ............. 8/115.6, 116 P, 188

[56] References Cited

U.S. PATENT DOCUMENTS

| | | | |
|---|---|---|---|
| 2,563,506 | 8/1951 | Werntz | 8/129 |
| 3,954,633 | 5/1976 | Dollinger et al. | 252/8.7 |

*Primary Examiner*—A. Lionel Clingman
*Attorney, Agent, or Firm*—Connolly and Hutz

[57] ABSTRACT

For fiber dressing an antistatic, heat-stable fiber lubricating agent, which contains a compound of the formula

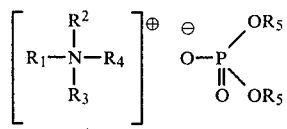

in which $R_1$ denotes a $C_8$–$C_{22}$ alkyl or alkenyl group, $R_2$ denotes a $C_8$–$C_{22}$ alkyl or alkenyl group or a $C_1$–$C_4$ alkyl group and $R_3$, $R_4$ and $R_5$ denote identical or different $C_1$–$C_4$ alkyl groups is used.

1 Claim, No Drawings

HEAT-STABLE QUATERNARY AMMONIUM COMPOUNDS FOR FIBER LUBRICATING

This application is a continuation of application Ser. No. 855,744 filed Nov. 29, 1977 now abandoned.

It is known that quaternary ammonium compounds are very suitable as antistatic components for fiber lubricating (Lindner, Tenside-Textilhilfsmittel Waschrohstoffe, [Surface-active Agents—Textile Auxiliaries—Detergent Raw Materials], volume II, page 1618). It is also known, however, that quaternary ammonium compounds which carry a hydrogen atom in the $\beta$-position to the nitrogen atom, decompose on heating with the formation of an olefine (Cram-Hammond Organic Chemistry 1959, page 399 et seq.). This reaction can already occur at 150° C. On the other hand, operations are nowadays carried out in the fiber industry at very high speeds, temperatures of up to 230° C. acting on the fiber. There is therefore a need for developing antistatic agents for fiber dressing of such a type that they have the good antistatic properties of the quaternary ammonium compounds but at the same time are also very heat-stable.

It has now been found that these conditions are fulfilled by those quaternary ammonium compounds which contain alkyl phosphate ions in place of the halide or alkyl sulphate counterions used hitherto. Thus, the invention relates to antistatic, heat-stable fiber lubricating agents which contain a compound of the formula 1

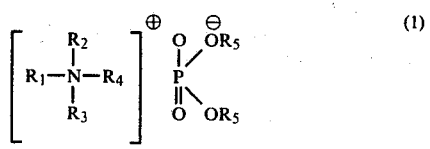

in which $R_1$ denotes an alkyl or alkenyl group having 8 to 22 C atoms, $R_2$ denotes an alkyl or alkenyl group having 8 to 22 C atoms or an alkyl group having 1-4 C atoms and $R_3$, $R_4$ and $R_5$ denote identical or different alkyl groups having 1-4 C atoms.

According to U.S. Pat. No. 2,563,506, these compounds are obtained by alkylation and quaternisation of secondary or tertiary amines of the formula

in which X represents a hydrogen atom or a group of the meaning of $R_3$, with trialkyl phosphates of the general formula

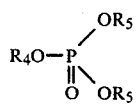

In the manufacture, the quaternary ammonium alkyl phosphates are obtained as more or less viscous oils or pastes. They can readily be dissolved in water, if necessary with the addition of lower alcohols. These compounds are marketed either as the 100% pure substance or as aqueous concentrates with a content of active substance of 40 to 100%. To apply them to the fiber, these concentrates are diluted with water to a content of 5–30 percent by weight. The application is carried out in the customary manner by dipping, spraying by means of godets or by means of pumps. The amount of active substance deposited on the fiber is in general 0.1–2, preferably 0.2–0.5, percent by weight. The quaternary ammonium alkyl phosphates of the formula 1 are suitable for use as lubricating agents, for example in the manufacture of filaments from synthetic fibers, such as polyester, polyacrylonitrole, polyamide and polyolefines, but also in the case of regenerated cellulose. They can be applied by themselves or together with other constituents of fiber lubricating agents, such as, for example, slip agents (mineral oils and ester oils) or emulsifiers (oxyethyllated fatty alcohols) or the like, to the fiber during the manufacture, for example during fixing and stretching processes, but also during further processing.

As a result of applying these compounds of the formula 1 during the manufacture and further processing, a very good reduction in the static charge of the fiber and a good softening and frictional effect are obtained. A particularly important fact is that these quaternary ammonium alkyl phosphates are very heat-stable and show no decomposition or yellowing phenomena even at temperatures above 200° C., although these compounds carry hydrogen atoms, which can be eliminated, in the $\beta$-position to the nitrogen atom. This result is also significant inasmuch as U.S. Pat. No. 2,563,506 merely mentions that compounds of this type are suitable as dispersing agents for mineral oil and as antistatic softeners for finished yarn. The question of heat stability does not arise in these fields of application.

EXAMPLE 1

Preparation of

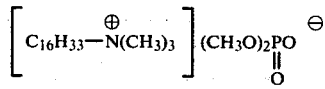

192 g (0.7 mole) of $C_{16}$-alkyldimethylamine and 101.5 g (0.7 mole) of trimethyl phosphate are brought together in a flask fitted with a stirrer and reflux condenser. The mixture is carefully heated, whilst stirring, to 100°–110° C. and held at this temperature for 2–2.5 hours. It is necessary to take great care that the temperature of 110° C. is not exceeded by the exothermic reaction. The degree of quaternisation is 98%.

The product is present as a viscous concentrate which can be diluted with 1:1 $H_2O$/i-propanol to a clear 50% strength solution.

EXAMPLE 2

Preparation of

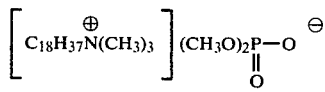

Analogously to Example 1, 210 g (0.5 mole) of stearyldimethylamine are reacted with 101.5 g (0.7 mole) of trimethylphosphate. The degree of quaternisation is 98%.

COMPARATIVE EXPERIMENTS

The following compounds are tested:

(a) Tallow fatty alkylpropylenediamine, fully quaternised with dimethyl sulphate (U.S. Pat. No. 3,954,633, Example 1 as a comparison (b) $C_{16}$-alkyltrimethylammonium chloride (comparison)

(c) Tallow fatty alkyltrimethylammonium chloride (comparison)

(d) Example 1 (according to the invention)

(e) Example 2 (according to the invention)

(f) $[C_{16}H_{33}-N^+(CH_3)_3]\,NO_3^-$ as a comparison

I. Heat stability and yellowing test (220° C./1 hour)

|   | Evaporation loss | Yellowing[1] |
|---|---|---|
| a | 9% | >1,100 |
| b | 15% | 900 |
| c | 6% | 900 |
| d (according to the invention) | 3% | 20 |
| e (according to the invention) | 2% | 20 |
| f | 7% | >1,100 |

[1]According to DIN 6,162; determination of the iodine color number

II. The products a–f are applied from aqueous solutions in an amount of about 0.7% of active substance by means of a godet to a PA6 filament (dtex 200 f 40) and the filaments are thermofixed for 1 minute at 185° C.

The friction on the filaments thus lubricated was determined in accordance with DT-OS No. 2,335,675. The following values of friction, antistatic properties and yellowing were measured:

|   | Friction | Antistatic properties[1] | Yellowing[2] |
|---|---|---|---|
| a | 0.380–0.445 | 5,000 | strong |
| b | 0.280–0.320 | 6,000 | strong |
| c | 0.275–0.320 | 5,800 | strong |
| d | 0.225–0.285 | 20 | trace |
| e | 0.220–0.280 | 25 | trace |
| f | 0.425–0.450 | 7,000 | strong |

[1]Antistatic values in meg-ohm (22° C./65% relative humidity)
[2]Visual assessment of the dressed filaments The following compounds were subjected to the heat stability test described above:

(a) Condensation product of stearic acid with diethylenetriamine (1:1 mole); fully quaternised with dimethyl sulphate (comparison according to DT-OS No. 2,335,675).

(b) Tallow fatty alkyltriethylammonium diethophosphate with $R_{tallow}=C_{14}-C_{18}$; main components $C_{16}H_{35}-$, $C_{18}H_{35}-$ and $C_{18}H_{37}-$.

(c) Distearylmethyl-dipropyl-ammonium dipropiophosphate.

(d) Tetradecyl/octadecyl-tributylammonium di-butophosphate.

(e) Soya alkyl-trimethyl-ammonium dimethophosphate. b,c,d and e: according to the invention Yellowing:

|   |   |
|---|---|
| a | >1,100 |
| b | 30 |
| c | 15 |
| d | 20 |
| e | 40 |

We claim:

1. A process for fiber lubricating during their manufacture wherein a compound of the formula

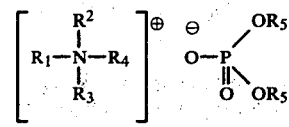

in which $R_1$ is $C_8-C_{22}$ alkyl or alkenyl, $R_2$ is $C_8-C_{22}$ alkyl or alkenyl or $C_1-C_4$ alkyl and $R_3$, $R_4$ and $R_5$ are identical or different $C_1-C_4$ alkyl is applied to the fibers.

* * * * *